US010245438B2

(12) United States Patent
Sato

(10) Patent No.: US 10,245,438 B2
(45) Date of Patent: Apr. 2, 2019

(54) AUTOMATED EXTERNAL DEFIBRILLATOR

(71) Applicant: NIHON KOHDEN CORPORATION, Shinjuku-ku, Tokyo (JP)

(72) Inventor: Masashi Sato, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 59 days.

(21) Appl. No.: 15/528,812

(22) PCT Filed: Feb. 4, 2016

(86) PCT No.: PCT/JP2016/000589
§ 371 (c)(1),
(2) Date: May 23, 2017

(87) PCT Pub. No.: WO2016/129258
PCT Pub. Date: Aug. 18, 2016

(65) Prior Publication Data
US 2017/0304640 A1    Oct. 26, 2017

(30) Foreign Application Priority Data
Feb. 12, 2015 (JP) ................. 2015-025206

(51) Int. Cl.
*A61N 1/00* (2006.01)
*A61N 1/39* (2006.01)
(Continued)

(52) U.S. Cl.
CPC ............ *A61N 1/3993* (2013.01); *A61N 1/046* (2013.01); *A61N 1/0492* (2013.01); *A61N 2001/083* (2013.01)

(58) Field of Classification Search
CPC .... A61N 1/046; A61N 1/0492; A61N 1/3993; A61N 2001/083
See application file for complete search history.

(56) References Cited

U.S. PATENT DOCUMENTS

D678,532 S    3/2013 Powers et al.
8,527,044 B2  9/2013 Edwards et al.
(Continued)

FOREIGN PATENT DOCUMENTS

| JP | 2005525200 A | 8/2005 |
| JP | 2012-232165 A | 11/2012 |
| WO | 2006067693 A1 | 6/2006 |

OTHER PUBLICATIONS

International Search Report dated May 18, 2016, issued by the International Searching Authority in counterpart International Application No. PCT/JP2016/000589 (PCT/ISA/210).
(Continued)

*Primary Examiner* — George Manuel
(74) *Attorney, Agent, or Firm* — Sughrue Mion, PLLC

(57) ABSTRACT

An automated external defibrillator includes a first pad at least partially colored in a first color, a second pad at least partially colored in a second color, and a main unit to which the first pad and the second pad are connected. The main unit has a first guidance surface that indicates how to attach of the first pad and the second pad. The first guidance surface has a first marker in the first color at a position corresponding to an attachment position of the first pad and a second marker in the second color at a position corresponding to an attachment position of the second pad.

15 Claims, 7 Drawing Sheets

(51) Int. Cl.
*A61N 1/04* (2006.01)
*A61N 1/08* (2006.01)

(56) References Cited

U.S. PATENT DOCUMENTS

| | | |
|---|---|---|
| 2003/0216785 A1 | 11/2003 | Edwards et al. |
| 2009/0254136 A1 | 10/2009 | Powers |
| 2013/0066390 A1* | 3/2013 | Schwibner ........... A61N 1/3993 607/7 |
| 2013/0345769 A1 | 12/2013 | Edwards et al. |
| 2015/0273224 A1 | 10/2015 | Powers et al. |

OTHER PUBLICATIONS

Written Opinion dated May 18, 2016, by the International Searching Authority in counterpart International Application No. PCT/JP2016/000589 (PCT/ISA/237).
Communication dated May 28, 2018, issued by the Japanese Patent Office in counterpart Japanese Patent Application No. 2015-025206.

* cited by examiner

[Fig. 1]
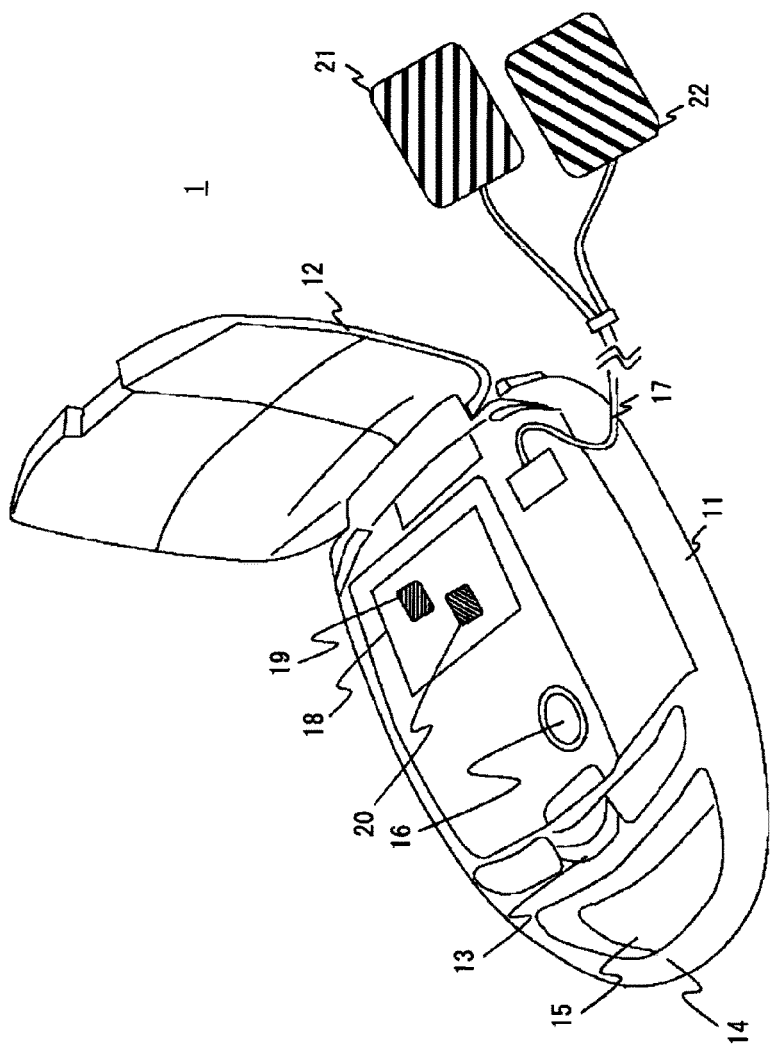

[Fig. 2]
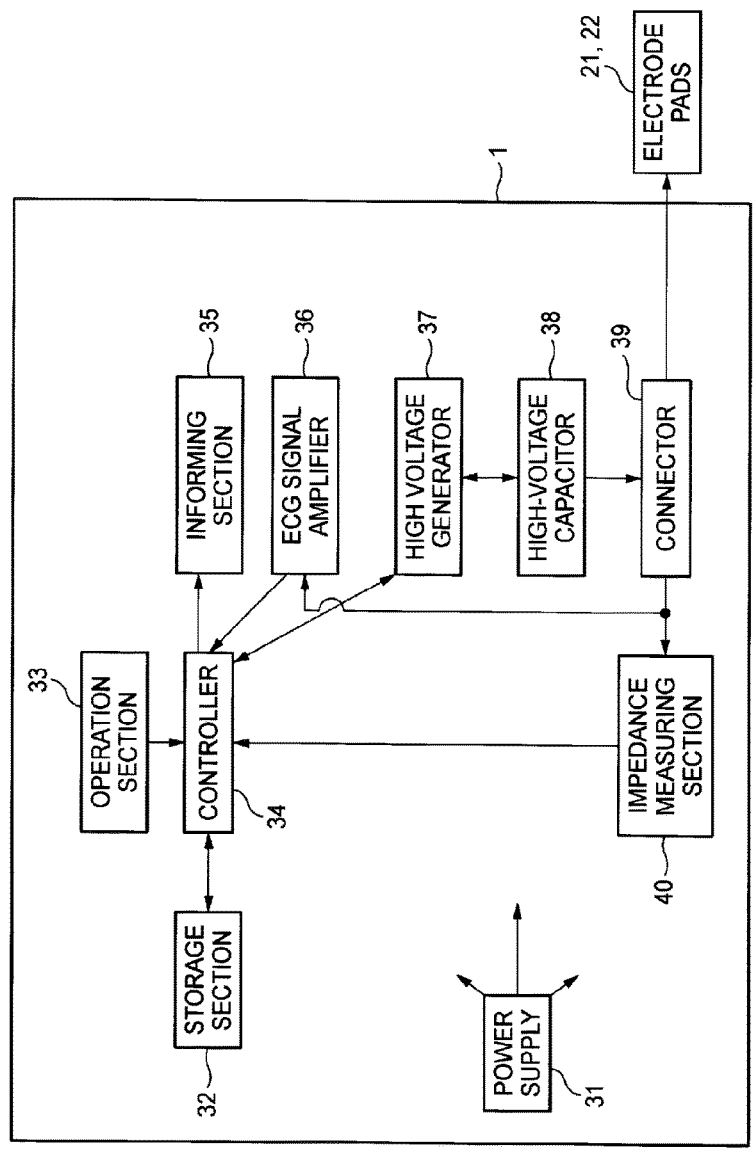

[Fig. 3]
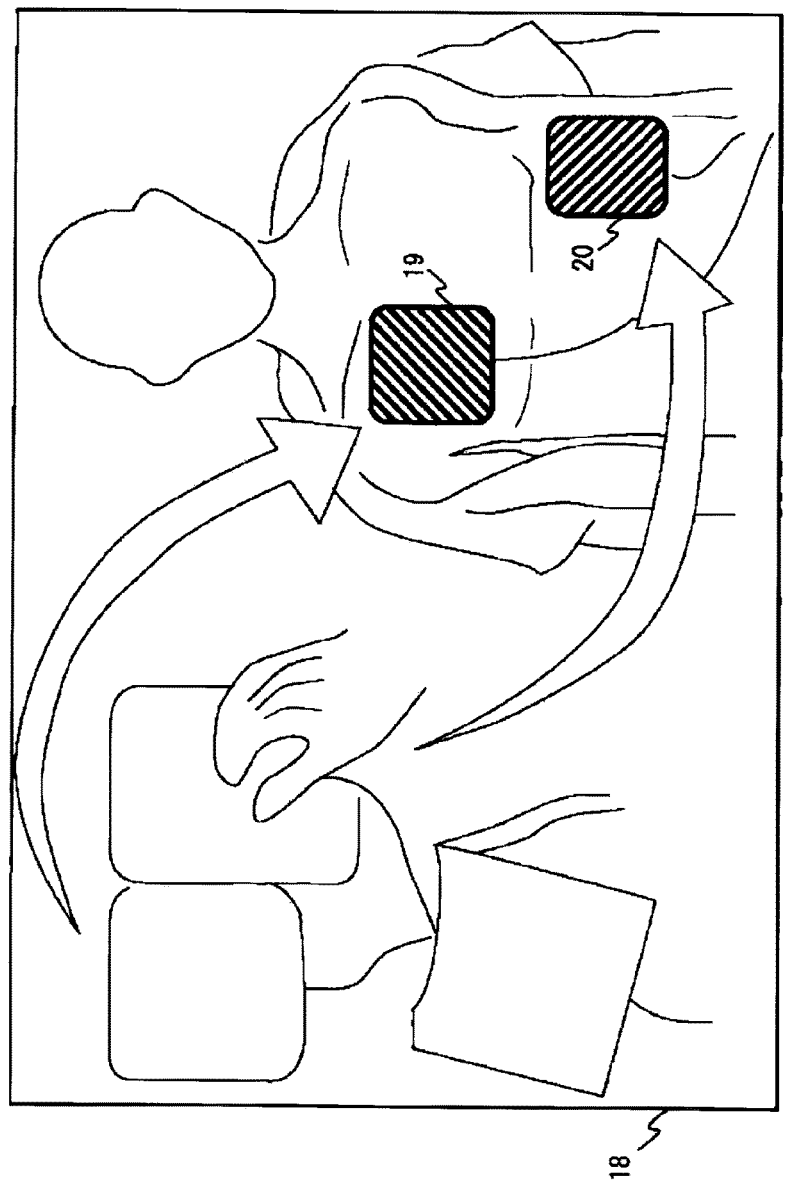

[Fig. 4A]

| ELECTRODE(S) | IMPEDANCE | INDICATOR |
|---|---|---|
| NOT ATTACHED (21, 22) | – | ON (19, 20) |
| ATTACHED (21) | NORMAL | OFF (19) |
| ATTACHED (22) | NORMAL | OFF (20) |

[Fig. 4B]

| ELECTRODE(S) | IMPEDANCE | INDICATOR |
|---|---|---|
| NOT ATTACHED (21, 22) | – | ON (19, 20) |
| ATTACHED (21, 22) | NORMAL | OFF (19, 20) |

[Fig. 4C]

| ELECTRODE(S) | IMPEDANCE | INDICATOR |
|---|---|---|
| NOT ATTACHED (21, 22) | – | OFF (19, 20) |
| ATTACHED (21) | NORMAL | ON (19) |
| ATTACHED (22) | NORMAL | ON (20) |

[Fig. 4D]

| ELECTRODE(S) | IMPEDANCE | INDICATOR |
|---|---|---|
| NOT ATTACHED (21, 22) | – | ON (19, 20) |
| ATTACHED (21) | NORMAL | OFF (19) |
| ATTACHED (21) | ABNORMAL | BLINK (19) |
| ATTACHED (22) | NORMAL | OFF (20) |
| ATTACHED (22) | ABNORMAL | BLINK (20) |

[Fig. 5]
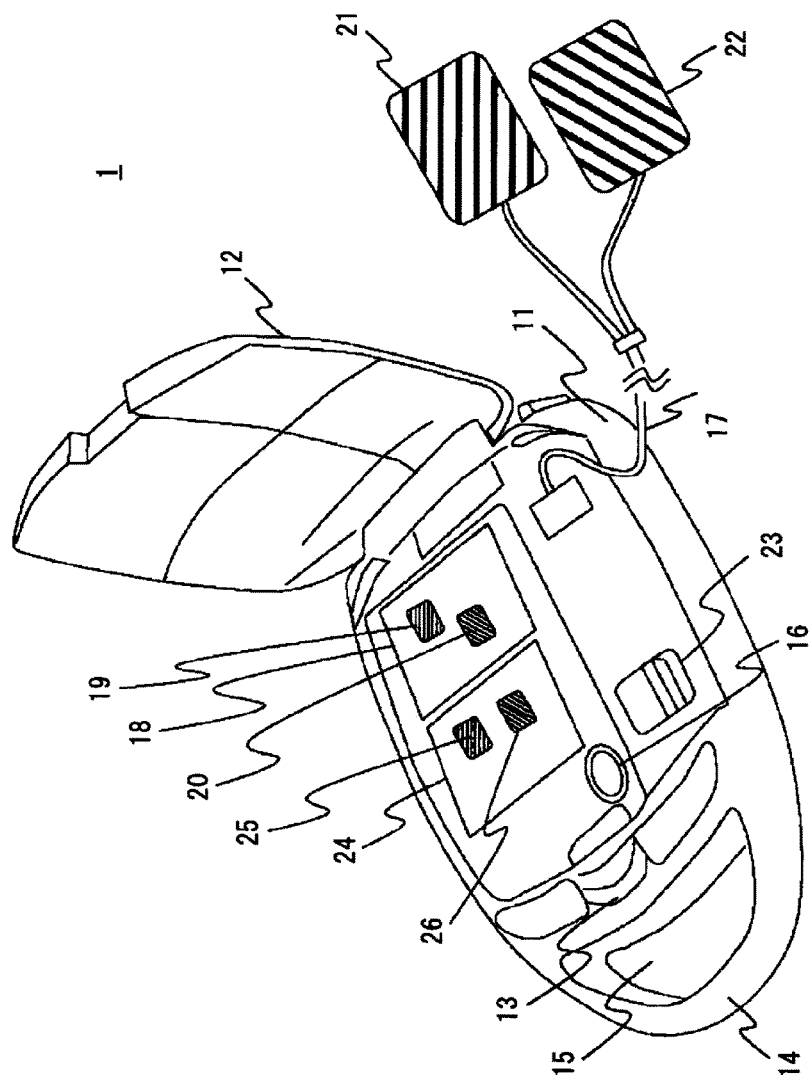

[Fig. 6]
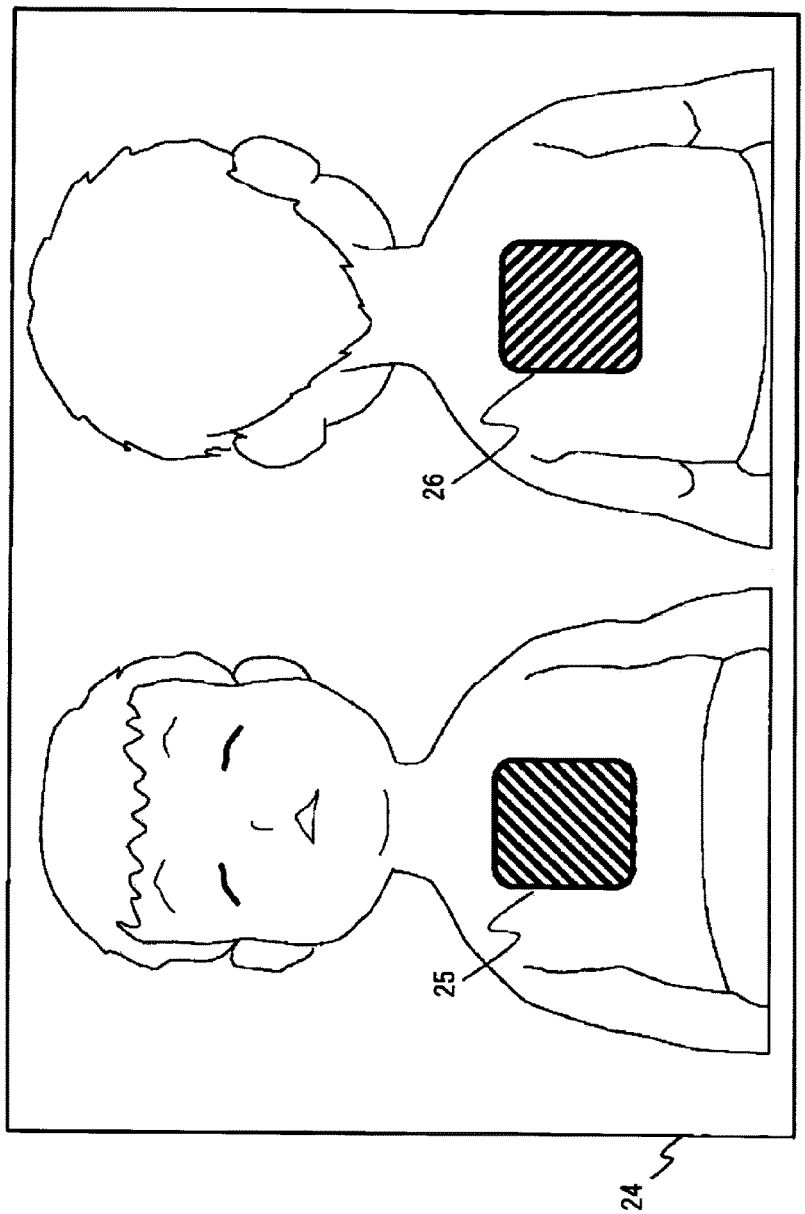

[Fig. 7]
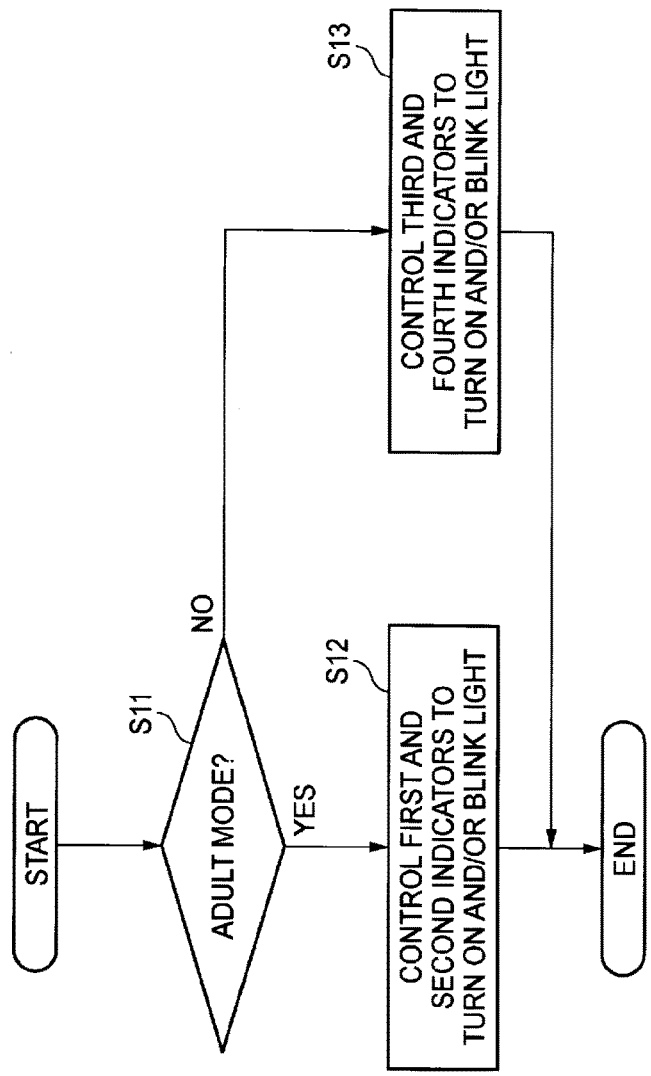

AUTOMATED EXTERNAL DEFIBRILLATOR

TECHNICAL FIELD

The presently disclosed subject matter relates to an automated external defibrillator (AED).

BACKGROUND ART

In recent years, AEDs have become popular, and can be found in various places such as commercial facilities and schools. The AEDs can automatically analyze ventricular fibrillation in a patient and, depending on a result of the analysis, cause the heart of a patient to recover its normal function by applying an electrical shock (i.e., defibrillation).

In using an AED, a user operates the AED by following verbal guidance output from the AED. Generally, operations to be performed by the user are mainly attachment of electrode pads and pressing of a defibrillation button. These operations themselves are not very difficult. However, the user is forced to perform the operations with almost no experience in an emergency situation where a patient is collapsed right in front. This is a very heavy psychological burden to the user.

In particular, a user is sometimes confused about the locations on the patient to which the electrode pads should be attached. In this connection, JP2005-525200A discloses an AED having an LED that is lit in green when the electrode pads are attached correctly and an LED that is lit in red when they are not.

The AED disclosed in JP2005-525200A allows a user to recognize whether or not the electrode pads are attached to a patient correctly. However, this AED does not allow, with the aid of colors or the like, a user to recognize the locations on a patient to which the respective electrode pads should be attached, and hence it is difficult for the user to recognize where to attach the electrode pads. Since an AED needs to be operated without a moment's delay, it is desirable that a user be able to attach the electrode pads quickly to correct locations on a patient.

SUMMARY

Illustrative aspects of the present invention provide an automated external defibrillator that allows a user to promptly attach electrode pads to a patient at correct positions.

According to an illustrative aspect of the present invention, an automated external defibrillator includes a first pad at least partially colored in a first color, a second pad at least partially colored in a second color, and a main unit to which the first pad and the second pad are connected. The main unit has a first guidance surface that indicates how to attach of the first pad and the second pad. The first guidance surface has a first marker in the first color at a position corresponding to an attachment position of the first pad and a second marker in the second color at a position corresponding to an attachment position of the second pad.

BRIEF DESCRIPTION OF DRAWINGS

FIG. 1 is a perspective view of an AED according to an exemplary embodiment of the present invention.

FIG. 2 is a block diagram illustrating an internal configuration of the AED.

FIG. 3 is a diagram illustrating an example of a first guidance surface of the AED.

FIG. 4A shows an example of indication patterns of indicators of the AED.

FIG. 4B shows another example of indication patterns of the indicators of the AED.

FIG. 4C shows another example of indication patterns of the indicators of the AED.

FIG. 4D shows another example of indication patterns of the indicators of the AED.

FIG. 5 is a perspective view of an AED according to another exemplary embodiment of the present invention.

FIG. 6 is a diagram illustrating an example of a second guidance surface of the AED shown in FIG. 5.

FIG. 7 is a flowchart of control operations executed by a controller of the AED shown in FIG. 5.

DESCRIPTION OF EMBODIMENTS

Hereinafter, exemplary embodiments of the present invention will be described in detail with reference to the drawings. However, the following exemplary embodiments do not limit the scope of the claimed invention. Further, sizes and proportions of the elements shown in the drawings are just for the purpose of illustration, and actual sizes and ratios may be different from those shown in the drawings.

FIG. 1 is a perspective view of an automated external defibrillator (AED) 1 according to an exemplary embodiment of the present invention. In FIG. 1, for the purpose of illustration, some elements (such as electrode pads 21, 22) are hatched by oblique lines.

The AED 1 has a main unit 11 (a main body of the AED 1) and a lid 12 that covers the main unit 11. The lid 12 is closed when the AED 1 is in storage. By closing the lid 12, dust and the like are prevented from entering the main unit 11.

The main unit 11 is provided with a tab 13, which can be slid by a user using, for example, his or her fingers. The AED 1 is rendered in an open state shown in FIG. 1 by the user's sliding the tab 13 toward a handle 14 using, for example, his or her fingers. Like common AEDs, the AED 1 has such a configuration that the main power (not shown) is turned on as soon as the lid 12 is opened.

The handle 14 is to be gripped by the user in carrying the AED 1. The handle 14 is formed adjacent to an opening 15 of the main unit 11.

A button 16 is an input interface for commanding that an electrical shock be applied to a patient. Like common AEDs, the AED 1 acquires an electrocardiogram and analyzes it automatically when the electrode pads 21, 22 are attached to the patient. If it is determined that an electrical shock should be applied to the patient based on the result of the analysis of the electrocardiogram, the AED 1 is made to be in a condition that allows the button 16 to be pressed (i.e., the AED 1 can receive an input from the user).

The button 16 may include an indicator (i.e., the button 16 itself can be lit and/or blinked). This is advantageous in that a user can press the button 16 while the button 16 is lit (meaning capable of applying an electrical shock to the patient) to apply the electrical shock to the patient.

A cable 17 connects the main unit 11 to the electrode pads 21, 22 electrically.

On a housing of the main unit 11, a first guidance surface 18 is provided. The first guidance surface 18 shows a guidance that teaches a user how to attach the electrode pads 21, 22. The first guidance surface 18 has a first indicator 19 and a second indicator 20.

The first indicator 19 (an example of a first marker) is colored in a first color (e.g., orange). That is, the first indicator 19 is a lamp or the like capable of being turned on and/or blinked in the first color. The first indicator 19 is turned on and/or blinked depending on an attachment condition of the electrode pad 21 to the patient (described later in detail with reference to FIGS. 4A to 4D). Instead of the first indicator 19, a mark (e.g., a patterned mark) that is colored in the first color may be provided on the first guidance surface 18 as the first marker. However, the indicator 19 is advantageous in that the lighting of the first indicator 19 allows the user to recognize, in addition to its attachment position, an attachment condition of the electrode pad 21.

The second indicator 20 (an example of a second marker) is colored in a second color (e.g., blue). That is, the second indicator 20 is a lamp or the like capable of being turned on and/or blinked in the second color. The second indicator 20 is turned on and/or blinked depending on an attachment condition of the electrode pad 21 to the patient (described later in detail with reference to FIGS. 4A to 4D). Instead of the second indicator 20, a mark (e.g., a patterned mark) that is colored in the second color may be provided on the first guidance surface 18. A specific example of a display on the first guidance surface 18 will be described later with reference to FIG. 3.

The electrode pad 21 (an example of first pad) is an electrode that is connected to the main unit 11 by the cable 17 and is to be attached to the chest of the patient. The contact surface, to contact the patient, of the electrode pad 21 is made of a self-adhesive substance, and the electrode pad 21 is attached to the patient by adhesion of this substance. At least part of the back surface, opposite to the contact surface, of the electrode pad 21 is colored in the first color. For example, the electrode pad 21 and the first indicator 19 are colored in orange.

The electrode pad 22 (an example of a second pad) is an electrode that is connected to the main unit 11 by the cable 17 and is to be attached to the chest of the patient. As in the case of the electrode pad 21, the contact surface, to contact the patient, of the electrode pad 22 is a seal surface, and the electrode pad 22 is attached to the patient by adhesion of this seal surface. At least part of the back surface, opposite to the contact surface, of the electrode pad 22 is colored in the second color. For example, the electrode pad 22 and the second indicator 20 are colored in blue.

The electrode pad 21 and the first indicator 19 both being the first color includes a situation where the electrode pad 21 and the first indicator 19 have similar colors. That is, it is considered that the electrode pad 21 and the first indicator 19 are both colored in the first color even if they are actually somewhat different from each other in color (e.g., in RGB values or luminance/lightness/chroma) as long as their colors allow the user to recognize that they correspond to each other. This also applies to the electrode pad 22 and the second indicator 20.

The first color and the second color are different from each other in such a degree that the user can recognize that they are different colors.

After the power of the AED 1 is turned on, the AED 1 outputs verbal guidance for urging the user to perform appropriate operations.

Next, the internal configuration (mainly electrical configuration) of the AED 1 will be described with reference to FIG. 2. The AED 1 has a power supply 31, a storage section 32, an operation section 33, a controller 34, an informing section 35, an ECG signal amplifier 36, a high voltage generator 37, a high-voltage capacitor 38, a connector 39, and an impedance measuring section 40.

The power supply 31 includes a battery, and supplies power to the individual processing units of the AED 1 by performing voltage conversion using a voltage control mechanism (not shown). The storage section 32 is provided to store programs that are necessary for operation of the AED 1, voice data, adjustment values, a measured electrocardiogram waveform, etc. The storage section 32 may be a secondary storage device such as a flash memory.

The operation section 33 is an interface through which a user operates the AED 1, and includes the tab 13 and the button 16 described above. The operation section 33 may also include an adult/child switch.

The controller 34 performs various controls of the AED 1. More specifically, the controller 34 performs an electrocardiogram analysis and various operation controls such as an energy charge/discharge control, a sequence control, and a voice output control. The controller 34 includes a central processing unit (CPU), a gate array, an A/D converter, etc.

The informing section 35 is controlled by the controller 34 to provide information to a user. The informing section 35 includes a speaker that outputs verbal guidance and indicators (including the first indicator 19 and the second indicator 20 described above).

The ECG signal amplifier 36 is configured to filter and amplify an electrocardiogram signal that is acquired through the electrode pads 21, 22 which are connected to the connector 39. The high voltage generator 37 charges and discharges energy to be used for electrical shock, under the control of the controller 34. The high-voltage capacitor 38 stores energy for electrical shock.

The impedance measuring section 40 measures impedances between body surfaces of the patient and the electrode pads 21, 22, and judges whether the electrode pads 21, 22 are attached to body surfaces on the basis of impedance variations. The impedance measuring section 40 may judge which of the electrode pads 21, 22 is attached to a body surface by, for example, referring to characteristic information (e.g., identification information buried in the electrode pad) of each of the electrode pads 21, 22. And the impedance measuring section 40 may judge whether or not each of the electrode pads 21, 22 is attached normally on the basis of a corresponding measured impedance value. The impedance measuring section 40 supplies measured impedance values of the respective electrode pads 21, 22 to the controller 34.

With the above configuration, the controller 34 switches the first indicator 19 so that it is turned on, blinking, or is turned off depending on a condition of attachment of the electrode pad 21 to the patient. That is, the first indicator 19 is lit, blinked, or turned off depending on a condition of attachment of the electrode pad 21 to the patient. Likewise, the controller 34 switches the second indicator 20 so that it is lit, blinked, or is turned off depending on a condition of attachment of the electrode pad 22 to the patient. That is, the second indicator 20 is lit, blinked, or turned off depending on a condition of attachment of the electrode pad 22 to the patient. Detailed examples of the controls for causing the first indicator 19 and the second indicator 20 to have their lights turned on, blinked, or turned off will be described later with reference to FIGS. 4A to 4D.

Next, the details of display on the first guidance surface 18 will be described with reference to FIG. 3. As mentioned above, the first guidance surface 18 visually informs a user how to attach the electrode pads 21, 22 to the patient, including where to attach the electrode pads 21, 22. In the example of FIG. 3, a figure of an upper body of a patient is shown on the first guidance surface 18. Generally, when using an AED, two electrode pads are placed such that the heart is interposed between the electrode pads (one electrode pad is placed on the right chest and the other on the left flank). The first indicator 19 and the second indicator 20 are provided to correspond to these positions of the electrode pads 21, 22, respectively. That is, the first indicator 19 is provided at a position corresponding to the attachment position of the electrode pad 21 (i.e., the right chest of the upper body of the patient). The second indicator 20 is provided at a position corresponding to the attachment position of the electrode pad 22 (i.e., the left flank of the upper body of the patient upper).

Examples of how the first indicator 19 and the second indicator 20 are turned on, blinked, and turned off will be described below. The first indicator 19 is turned on when the power of the AED 1 is turned on. The first indicator 19 is lit in the same color (the first color) as the color of the electrode pad 21. The first indicator 19 is turned off when the electrode pad 21 is attached to the patient and a measured impedance has a normal value. A detection of attachment of the electrode pad 21 and an impedance measurement are performed by the controller 34 in a similar manner as in general AEDs. Like the first indicator 19, the second indicator 20 is lit in the same color (the second color) as the color of the electrode pad 22 and turned off in a similar manner as the first indicator 19. The arrows shown in FIG. 3 may also be configured as similar indicators.

The indication patterns of the first indicator 19 and the second indicator 20 are not limited to the above-described pattern as long as the manners of their display are switched according to the states of the electrode pads 21, 22. FIGS. 4A to 4D show some examples of indication patterns of the first indicator 19 and the second indicator 20. The numbers shown in FIGS. 4A to 4D correspond to the reference numerals used in FIG. 1.

According to the indication patterns of FIG. 4A, the controller 34 turns on the first indicator 19 and the second indicator 20 when the power of the AED 1 is turned on and neither of the electrode pads 21, 22 is attached to the patient. The controller 34 turns off the first indicator 19 when the electrode pad 21 is attached and a measured impedance of the electrode pad 21 is normal. The controller 34 turns off the second indicator 20 when the electrode pad 22 is attached and a measured impedance of the electrode pad 22 is normal.

According to the indication patterns of FIG. 4B, the controller 34 turns on the first indicator 19 and the second indicator 20 when the power of the AED 1 is turned on and neither of the electrode pads 21, 22 is attached to the patient. The controller 34 turns off the first indicator 19 and the second indicator 20 when both of the electrode pads 21, 22 are attached and both of their measured impedance values are normal. That is, the controller 34 may be configured to cause both the first indicator 19 and the second indicator 20 to have their lights turned on, blinked, or turned off, based on whether both of the electrode pads 21, 22 are attached normally.

The indication patterns of FIG. 4C is reverse to that of FIG. 4A. The controller 34 turns off the first indicator 19 and the second indicator 20 when the power of the AED 1 is turned on and neither of the electrode pads 21, 22 is attached to the patient. The controller 34 turns on the first indicator 19 when the electrode pad 21 is attached and a measured impedance of the electrode pad 21 is normal. The controller 34 turns on the second indicator 20 when the electrode pad 22 is attached and a measured impedance of the electrode pad 22 is normal.

FIG. 4D shows another example of indication patterns in which the first indicator 19 and the second indicator 20 are controlled to be turned on/off or blinked in view of not only their attachment conditions but also their measured impedance values. The controller 34 turns on the first indicator 19 and the second indicator 20 when the power of the AED 1 is turned on and neither of the electrode pads 21, 22 is attached to the patient. The controller 34 turns off the first indicator 19 when the electrode pad 21 is attached and the measured impedance of the electrode pad 21 is normal. The controller 34 blinks the first indicator 19 when the electrode pad 21 is attached but the measured impedance of the electrode pad 21 is abnormal. The controller 34 turns off the second indicator 20 when the electrode pad 22 is attached and the measured impedance of the electrode pad 22 is normal. The controller 34 blinks the second indicator 20 when the electrode pad 22 is attached but the measured impedance of the electrode pad 22 is abnormal.

The indication patterns shown in FIGS. 4A to 4D are merely examples and the controller 34 may perform controls in a different manner.

For example, the impedance measuring section 40 may detect a difference between measured impedance values of the electrode pads 21, 22. The impedance measuring section 40 determines that both of the electrode pads 21, 22 are attached if the difference between measured impedance values of the electrode pads 21, 22 is smaller than or equal to a certain value. If it is determined that both of the electrode pads 21, 22 are attached, the controller 34 switches the first indicator 19 and the second indicator 20 from a turned-on condition to a turned-off condition (or from the turned-off condition to the turn-one condition). That is, the first indicator 19 and the second indicator 20 may be lit, blinked, or turned off in accordance with whether the difference between measured impedance values of the electrode pads 21, 22 is smaller than or equal to a certain value.

Next, advantages of the AED 1 according to the present exemplary embodiment will be described. In the exemplary embodiment, the electrode pads 21, 22 are colored in different colors. The first marker (first indicator 19) and the second marker (second indicator 20) which are colored in the colors corresponding to the colors of the electrode pads 21, 22, respectively, are provided on the first guidance surface 18 at the positions corresponding to the attachment positions of the electrode pads 21, 22, respectively. As a result, by referring to the colors and positions of the respective markers on the first guidance surface 18, a user can easily recognize the positions to which the respective electrode pads 21, 22 should be attached. Thus, the user can promptly attach the electrode pads 21, 22 at the correct positions on the patient without being confused.

Since the first indicator 19 on the first guidance surface 18 is lit, blinked, or turned off depending on an attachment condition of the electrode pad 21, the user can easily recognize the attachment condition of the electrode pad 21. Likewise, since the second indicator 20 on the first guidance surface 18 is lit, blinked, or turned off depending on an attachment condition of the electrode pad 22, the user can easily recognize the attachment condition of the electrode pad 22. Where as shown in FIG. 4B both of the first indicator 19 and the second indicator 20 are turned off when both of the electrode pads 21, 22 are attached correctly, the user can easily recognize the timing at which the two electrode pads 21, 22 are successfully attached.

It is preferable that the back surface, opposite to the contact surface (adhesive surface) that contacts a patient, of the electrode pad 21 be colored in the first color. By coloring, in the first color, the back surface of the electrode pad 21 which is the surface to be observed by the user, the user can recognize an attachment position of the electrode pad 21 more easily. Likewise, it is preferable that the back surface, opposite to the contact surface (adhesive surface) to contact a patient, of the electrode pad 22 be colored in the second color.

FIG. 5 is a perspective view showing an AED 1 according to another exemplary embodiment of the present invention. This AED 1 has guidance surfaces to be switched by an adult/child switch. In the following description, elements denoted by the same reference numerals as those of the foregoing exemplary embodiment have the same functions and structures as those of the foregoing exemplary embodiment unless otherwise specified.

The AED 1 shown in FIG. 5 has, in addition to the elements of the AED 1 shown in FIG. 1, an adult/child switch 23 and a second guidance surface 24. The adult/child switch 23 is provided to switch an electrical shock between an adult mode and a child mode, as provided in general AEDs. A user performs a manual switching on the adult/child switch 23 when necessary. Instead of the adult/child switch 23, the AED 1 may have other means for switching between the adult mode and the child mode, such as a child key or the like.

The second guidance surface 24 has a third indicator 25 (an example of a third marker) and a fourth indicator 26 (fourth marker). The second guidance surface 24 shows a guidance that teaches to a user how to attach the electrode pads 21, 22 to a child.

The third indicator 25 (third marker) is colored in the first color (e.g., orange). That is, the third indicator 25 is a lamp or the like capable of being lit and/or blinked in the first color. The third marker may be a mark or the like that is colored in the first color.

The fourth indicator 26 (an example of a fourth marker) is colored in the second color (e.g., blue). That is, the fourth indicator 26 is a lamp or the like capable of being lit and/or blinked in the second color. The fourth marker may be a mark or the like that is colored in the second color.

In the exemplary embodiment, the first indicator 19 and the third indicator 25 are correlated with the electrode pad 21. In other words, the first indicator 19, the third indicator 25, and the electrode pad 21 are colored in the first color. Likewise, the second indicator 20 and the fourth indicator 26 are correlated with the electrode pad 22. In other words, the second indicator 20, the fourth indicator 26 and the electrode pad 22 are colored in the second color.

Next, the details of display on the second guidance surface 24 will be described with reference to FIG. 6. As mentioned above, the second guidance surface 24 visually teaches how to attach the electrode pads 21, 22 to a child patient, including where to attached the electrode pads 21, 22. In the example of FIG. 6, a chest side and a back side of an upper body of a child are shown on the second guidance surface 24. Generally, when using an AED on a child, one of the electrode pads is placed on a chest and the other electrode pad is placed on a back of the child. The third indicator 25 and the fourth indicator 26 are provided so as to correspond to these locations. That is, the third indicator 25 is provided at a position corresponding to the attachment position of the electrode pad 21 (i.e., the chest side of a child) and the fourth indicator 26 is provided at a position corresponding to the attachment position of the electrode pad 22 (i.e., the back side of a child).

The indicators to be lit, blinked, or turned off are switched in accordance with the switching of the adult/child switch 23. A display control to be executed by the controller 34 will be described below with reference to FIG. 7. When the power of the AED 1 is turned on or the adult/child switch 23 is switched, the controller 34 detects whether the patient is an adult or a child based on an input from the adult/child switch 23 (S11). If the patient is an adult (S11: yes), the controller 34 controls the first indicator 19 and the second indicator 20 to turn on and/or blink light (S12). On the other hand, if the patient is a child (S11: no), the controller 34 controls the third indicator 25 and the fourth indicator 26 to turn on and/or blink light (S13). The lighting/blinking control methods may be the same as in the first exemplary embodiment (see FIG. 3).

According to the exemplary embodiment described above, the AED 1 has the second guidance surface 24 for the child mode in addition to the first guidance surface 18 for the adult mode. The guidance surface to have the lights turned on or blinking is switched in accordance with the switching of the adult/child switch 23. That is, when the patient is an adult, the first indicator 19 and the second indicator 20 provided in the first guidance surface 18 are turned on or blinked. When the patient is a child, the third indicator 25 and the fourth indicator 26 provided in the second guidance surface 24 are lit or blinked. Therefore, a user can easily recognize the attachment positions of the electrode pads 21, 22 irrespective of whether the patient is an adult or a child.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

For example, the first guidance surface 18 and the second guidance surface 24 may be provided on the lid 12 side rather than on the main unit 11 side.

Verbal guidance may be output so as to be timed with display (turning on, blinking, turning-off of light) of the first indicator 19 and the second indicator 20 on the first guidance surface 18.

The main unit 11 and the pair of electrode pads 21, 22 may be manufactured and/or sold separately. That is, the main unit 11 may be configured to be connectable to the electrode pads 21, 22 and to have the first marker and the second marker that are colored in different colors that correspond to the colors of the electrode pads 21, 22, respectively.

This application is based on Japanese Patent Application No. 2015-025206 filed on Feb. 12, 2015, the entire content of which is incorporated herein by reference.

The invention claimed is:

1. An automated external defibrillator comprising:
a first pad at least partially colored in a first color;
a second pad at least partially colored in a second color; and
a main unit to which the first pad and the second pad are connected, the main unit comprising a first guidance surface indicating how to attach the first pad and the second pad,
wherein the first guidance surface comprises a first marker comprising an first indicator capable of being turned on and/or blinked in the first color at a position corresponding to an attachment position of the first pad and a second marker comprising a second indicator capable of being turned on and/or blinked in the second color at a position corresponding to an attachment position of the second pad.

2. The automated external defibrillator according to claim 1, wherein lighting, blinking and turning off of the first indicator and the second indicator are switched in accordance with whether a difference between impedance values of the first pad and the second pad is smaller than or equal to a certain value.

3. The automated external defibrillator according to claim 1, wherein lighting, blinking and turning off of the first indicator are switched in accordance with a condition of attachment of the first pad to a patient.

4. The automated external defibrillator according to claim 3, wherein the first indicator is lit when a power of the automated external defibrillator is turned on, and is turned off when the first pad is correctly attached to the patient.

5. The automated external defibrillator according to claim 1, wherein lighting, blinking and turning off of the second indicator are switched in accordance with a condition of attachment of the second pad to a patient.

6. The automated external defibrillator according to claim 5, wherein the second indicator is lit when a power of the automated external defibrillator is turned on, and is turned off when the second pad is correctly attached to the patient.

7. The automated external defibrillator according to claim 1, wherein lighting, blinking and turning off of the first indicator and the second indicator are switched in accordance with whether both of the first pad and the second pad are correctly attached to a patient.

8. The automated external defibrillator according to claim 1, wherein a back surface, opposite to a surface that contacts a patient, of the first pad is colored in the first color and a back surface, opposite to a surface that contacts the patient, of the second pad is colored in the second color.

9. The automated external defibrillator according to claim 1, wherein the main unit further comprises a second guidance surface indicating how to attach the first pad and the second pad to a child, and
wherein the second guidance surface comprises a third marker colored in the first color at a position corresponding to an attachment position of the first pad and a fourth marker colored in the second color at a position corresponding to an attachment position of the second pad.

10. The automated external defibrillator according to claim 9, wherein the third marker comprises a third indicator capable of being lit or blinked, and wherein one of the first indicator and the third indicator is lit, blinked, or turned off in accordance with a condition of attachment of the first pad to a patient and based on an input from an adult/child switching interface.

11. The automated external defibrillator according to claim 1, further comprising:
an impedance measuring section which is configured to detect attachment of the first pad to a patient from an impedance value between the first pad and a body surface of the patient,
wherein lighting, blinking and turning off of the first indicator are controlled so as to be different from each other depending on cases that are a first case where the first pad is not attached to the patient, a second case where the first pad is attached to the patient and the impedance value is normal, and a third case where the first pad is attached to the patient and the impedance value is abnormal.

12. The automated external defibrillator according to claim 11, wherein the impedance measuring section is configured to detect attachment of the second pad to the patient from an impedance value between the second pad and the body surface of the patient, and
wherein lighting, blinking and turning off of the second indicator are controlled so as to be different from each other depending on cases that are a fourth case where the second pad is not attached to the patient, a fifth case where the second pad is attached to the patient and the impedance value is normal, and a sixth case where the second pad is attached to the patient and the impedance value is abnormal.

13. An automated external defibrillator comprising:
a main unit to which a first pad and a second pad are connectable, the main unit comprising a first guidance surface indicating how to attach the first pad at least partially colored in a first color and the second pad at least partially colored in a second color,
wherein the first guidance surface comprises a first indicator capable of being turned on and/or blinked in the first color at a position corresponding to an attachment position of the first pad and a second indicator capable of being turned on and/or blinked in the second color at a position corresponding to an attachment position of the second pad.

14. The automated external defibrillator according to claim 13, further comprising:
an impedance measuring section which is configured to detect attachment of the first pad to a patient from an impedance value between the first pad and a body surface of the patient,
wherein lighting, blinking and turning off of the first indicator are controlled so as to be different from each other depending on cases that are a first case where the first pad is not attached to the patient, a second case where the first pad is attached to the patient and the impedance value is normal, and a third case where the first pad is attached to the patient and the impedance value is abnormal.

15. The automated external defibrillator according to claim 14, wherein the impedance measuring section is configured to detect attachment of the second pad to the patient from an impedance value between the second pad and the body surface of the patient, and
wherein lighting, blinking and turning off of the second indicator are controlled so as to be different from each other depending on cases that are a fourth case where the second pad is not attached to the patient, a fifth case where the second pad is attached to the patient and the impedance value is normal, and a sixth case where the second pad is attached to the patient and the impedance value is abnormal.

* * * * *